United States Patent [19]

Bowler

[11] 3,933,438
[45] Jan. 20, 1976

[54] COMBUSTIBLE GAS SENSOR FOR CLOSED LOOP FUEL CONTROL

[75] Inventor: Lauren L. Bowler, Bloomfield Hills, Mich.

[73] Assignee: General Motors Corporation, Detroit, Mich.

[22] Filed: July 5, 1974

[21] Appl. No.: 485,913

[52] U.S. Cl. ............... 23/255 R; 23/254 R; 60/276; 123/119 R; 123/119 E; 123/140 MC
[51] Int. Cl.² .................... F02M 7/12; G01N 31/10; G01N 33/22
[58] Field of Search .......... 23/254 R, 255 R, 232 R; 60/276; 123/119 E

[56] References Cited
UNITED STATES PATENTS

| | | | |
|---|---|---|---|
| 1,959,242 | 5/1934 | Kennedy | 23/255 R |
| 2,263,335 | 11/1941 | Heinz | 23/255 R X |
| 2,449,067 | 9/1948 | Guillemin, Jr. | 23/254 R X |
| 3,314,281 | 4/1967 | Reece et al. | 23/254 X |
| 3,730,157 | 5/1973 | Gerhold | 60/276 UX |

Primary Examiner—Joseph Scovronek
Attorney, Agent, or Firm—Robert M. Sigler

[57] ABSTRACT

A combustible gas sensor for use in a closed loop fuel control system for a combustion engine comprises a pair of sensor conduits within the main exhaust conduit of the engine, with exhaust gas drawn through one of the sensor conduits and a mixture of exhaust gas and air drawn through the other by engine induction vacuum at controlled rates. A catalyst coated capillary tube within each secondary conduit has air drawn through it at a constant rate. On account of the catalytically induced combustion on its outer surface, the capillary tube exposed to the air-exhaust mixture heats more than the other by an amount dependent upon the concentration of combustible gas in the exhaust. The capillary tubes are connected in series; and the pressure at the junction, when compared with a reference, is a function of the combustible gas concentration. The use of two capillary tubes in each conduit connected in a "bridge" configuration eliminates the need for a separately generated reference pressure.

1 Claim, 7 Drawing Figures

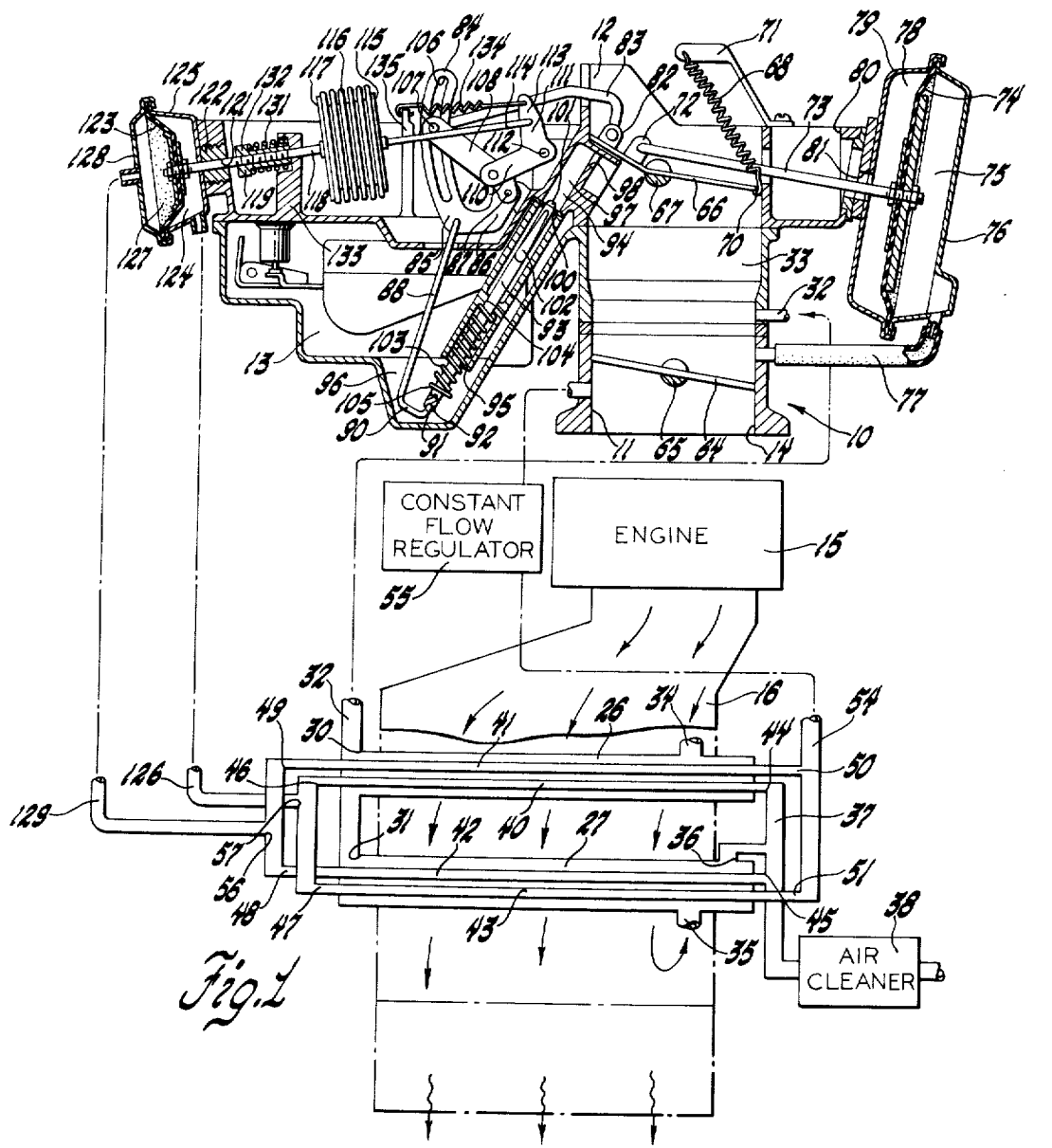
*Fig.1*
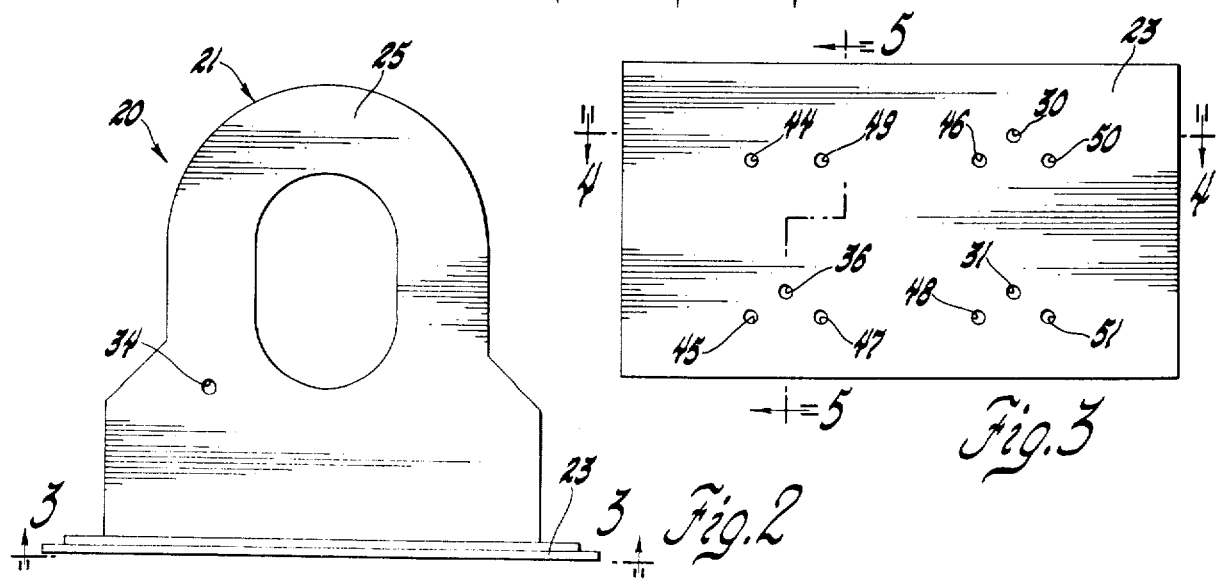
*Fig.2*   *Fig.3*

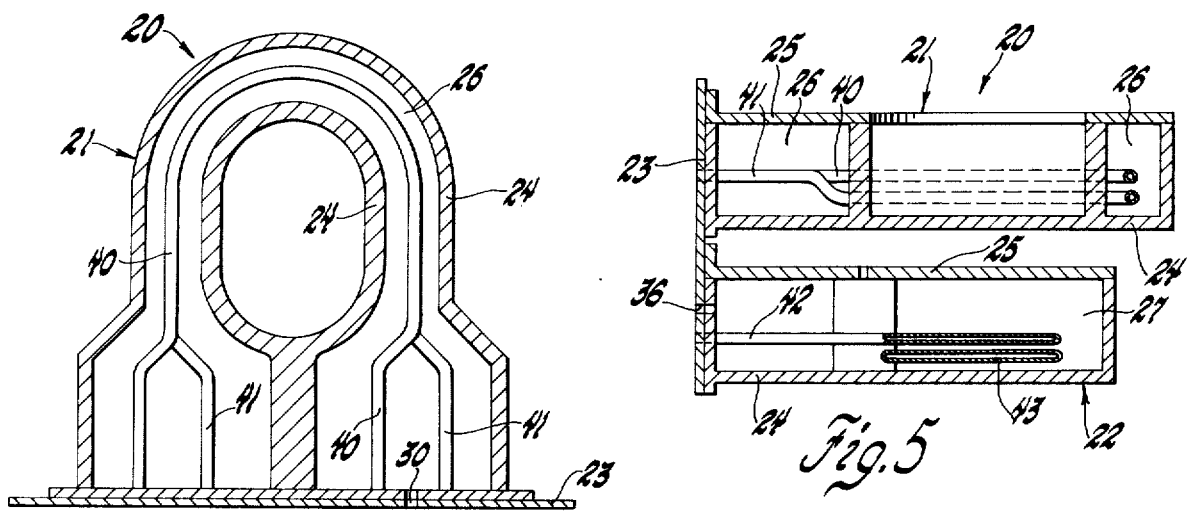
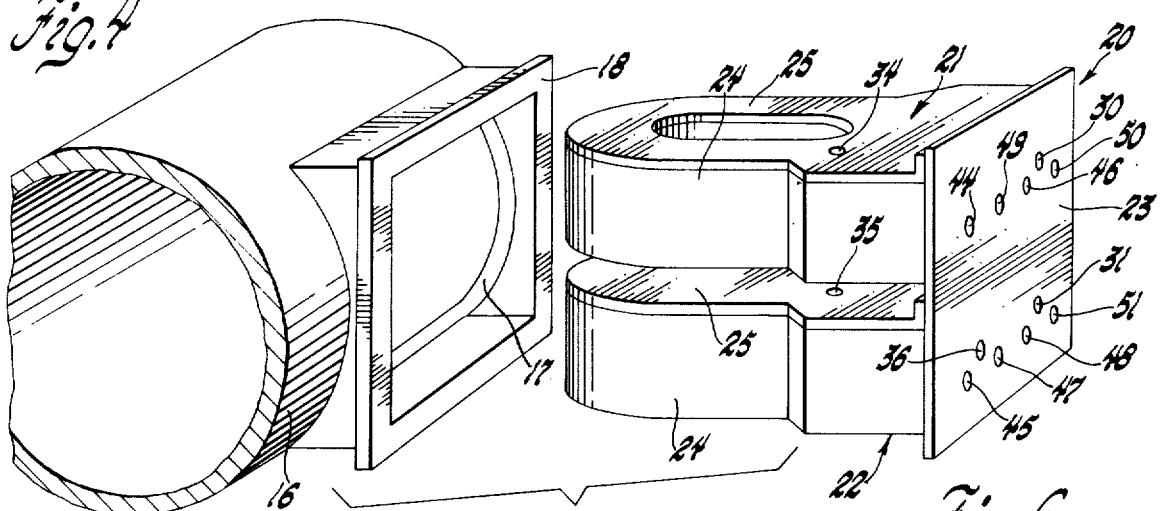
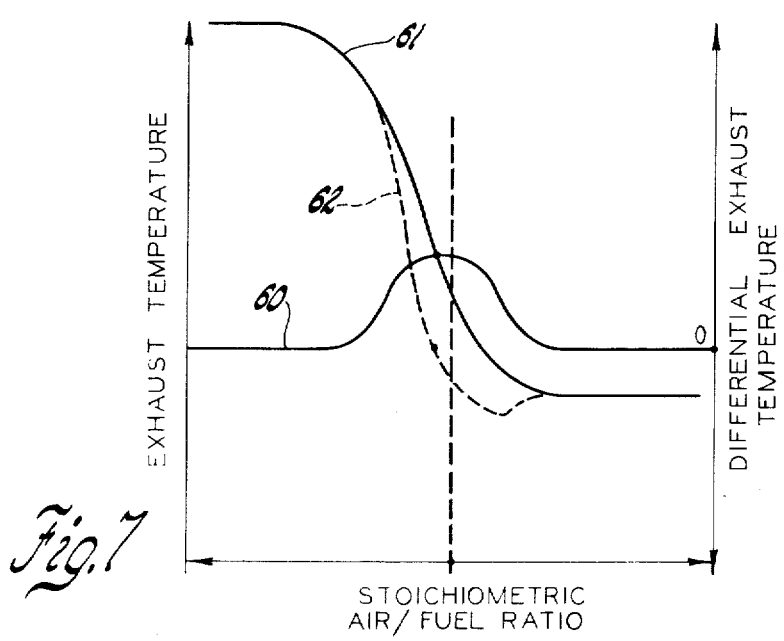

3,933,438

COMBUSTIBLE GAS SENSOR FOR CLOSED LOOP FUEL CONTROL

SUMMARY OF THE INVENTION

My invention relates to systems that control the input air-fuel mixture to a combustion engine in order to minimize undesirable emissions in the engine exhaust. It relates in particular to a closed loop fuel control system using a combustible gas sensor in the exhaust system to provide a feedback control signal.

Catalytic devices for inducing chemical changes in certain constituents of engine exhaust gases are well known. One type of catalyst induces oxidation of carbon monoxide and unburned hydrocarbons to carbon dioxide and water; while another kind induces reduction of oxides of nitrogen to nitrogen and oxygen. Often both types of catalysts are needed to meet all emission goals for a particular engine.

It is generally known that a single catalytic device containing both types of catalyst can be used if the air-fuel ratio of the fuel mixture fed to the engine is kept at a constant ratio just slightly on the rich side of stoichiometric, since at this point the emission levels of all three major undesirable exhaust constituents are reasonably low. The air-fuel ratio must be maintained quite closely: oxides of nitrogen increase sharply as the mixture crosses to the lean side of stoichiometric; and carbon monoxide increases rapidly as the mixture becomes more rich. Standard open loop fuel controls cannot maintain the air-fuel mixture with sufficient precision to take advantage of this situation.

A closed loop system, using a sensor device sensitive to some fuel or exhaust parameter to provide a feedback control signal to the fuel induction system, will provide sufficient control over the air-fuel mixture to keep it within the desired range. An important part of such a system, of course, is a suitable sensor.

My sensor is generally of the type wherein the difference in temperature between a catalytic bed exposed to exhaust gases and another catalytic bed exposed to a mixture of exhaust gases and excess air is measured to produce a signal that is a function of the concentration of combustible gas in the exhaust gases. Over a certain range of air-fuel ratio, such a differential temperature varies predictably with air-fuel ratio to provide a useful feedback signal.

In particular, my sensor uses a number of capillary tubes having fluid drawn through them at a constant rate to provide a pressure analogue of the temperature. This pressure can be applied directly to a differential pressure motor connected to air-fuel ratio changing apparatus in a carburetor or fuel injection system.

Further details and advantages of my invention will be apparent in the accompanying Figures and following description of the preferred embodiment.

SUMMARY OF THE DRAWINGS

FIG. 1 is a schematic diagram of my invention in its environment.

FIG. 2 is a top view of a preferred embodiment of my invention.

FIG. 3 is a view along line 3—3 in FIG. 2.

FIG. 4 is a view along line 4—4 in FIG. 3.

FIG. 5 is a view along line 5—5 in FIG. 3.

FIG. 6 is an exploded perspective view of my invention in its environment.

FIG. 7 is a graphical representation of the relationship between the differential temperature in my invention and air-fuel ratio.

DESCRIPTION OF THE PREFERRED EMBODIMENT

Referring to FIG. 1, an air valve carburetor, generally indicated as 10, has an induction bore 11 in which air admitted through an air inlet 12 is mixed in a controlled ratio with fuel from a fuel reservoir 13 and delivered through an outlet 14 to a combustion engine 15. The exhaust gases from the engine 15 enter an exhaust system comprising a main exhaust conduit 16, a portion of which is also shown in FIG. 6. A portion of the wall of the main exhaust conduit 16 is cut out to form a window 17; and around the window 17 is welded a mounting bracket 18.

As seen most clearly in FIG. 6, a sensor assembly 20 comprises an upper sensor bed 21 and a lower sensor bed 22 fixed perpendicularly to a mounting plate 23. The mounting plate 23 is adapted to be fixed and sealed to the mounting bracket 18 with the sensor beds 21 and 22 projecting into the main exhaust conduit 16.

Each of the sensor beds 21 and 22 comprise identical lower housings 24 closed by identical cover plates 25. These parts form a sensor conduit 26 in upper sensor bed 21 and a sensor conduit 27 in lower sensor bed 22. The sensor conduits 26 and 27 are identical in size and shape, each being generally U-shaped with the two ends of the U against the mounting plate 23, as seen in FIG. 4.

An outlet opening 30 through the mounting plate 23 opens to one end of the sensor conduit 26; likewise outlet opening 31 through mounting plate 23 opens to the corresponding end of sensor conduit 27. Openings 30, 31 and others yet to be described through plate 23 are shown in FIGS. 3 and 6 and are indicated schematically in FIG. 1. As shown in FIG. 1, a vacuum conduit 32 connects each of the sensor conduits through its outlet opening 30 or 31 to a mixing region 33 in the induction bore 11 which, as will be explained later, is maintained at a substantially constant pressure below atmospheric pressure.

Near the other end of sensor conduits 26 and 27, exhaust inlets 34 and 35, respectively, are formed through the cover plates 25, as shown in FIG. 6. Exhaust inlets 34 and 35 open the interior of the sensor conduits 26 and 27, respectively, to the interior of the main exhaust conduit 16. In addition, an air inlet opening 36 through mounting plate 23 communicates the same end of sensor conduit 27 only to the atmosphere through an air inlet conduit 37 and an air cleaner 38, shown in FIG. 1.

The engine induction vacuum present in mixing chamber 33 causes exhaust gases to be drawn through sensor conduit 26 from exhaust inlet 34 to outlet opening 30 and a mixture of exhaust gases and air to be drawn through sensor conduit 27 from exhaust inlet 35 and air inlet 36 to outlet 31. Exhaust inlets 34 and 35 and air inlet 36 are all orifices whose diameter is chosen to produce substantially equivalent mass flow rates through the sensor conduits and establish a desirable air-exhaust ratio in sensor conduit 27. In tests, satisfactory results were obtained with a flow through sensor conduit 27 of two CFH air to 16.5 CFH exhaust gas.

In this preferred embodiment, each of the sensor conduits 26 and 27 contains a pair of capillary tubes, numbered from top to bottom in FIGS. 5, 40, 41 42 and 43. Each of the capillary tubes 40–43 is a stainless steel tube with an inner diameter that is small in relation to its length. Typical dimensions for such a tube are: outer diameter, 0.062 inch; inner diameter, 0.028 inch; and length, approximately six to seven inches. With a fixed length and diameter, and assuming constant laminar flow through the tube, the differential pressure across the tube is in direct proportion to the fluid's viscosity, which is a function of temperature. Thus each capillary tube generates a differential pressure signal which is a function of its temperature.

The capillary tubes 40–43 are each bent into a generally U-shaped configuration to conform with the shape of sensor conduits 26 and 27 and are further bent as shown in FIGS. 4 through 6 so that their ends can be mounted side by side in the mounting plate 23 but a substantial portion of each will be vertically aligned. Each of the tubes 40–43 is coated on its outer surface with an oxidation catalyst material in order to induce oxidation in the gases flowing over and around it.

The ends of tubes 40–43 open through the mounting plate 23 are interconnected with each other and additional conduits. Referring to FIGS. 1 and 6, the inlet end 44 of tube 40 and inlet end 45 of tube 42 are each open to the air inlet conduit 37; the outlet end 46 of tube 40 is connected to the inlet end 47 of tube 43; the outlet end 48 of tube 42 is connected to the inlet end 49 of tube 41; and the outlet end 50 of tube 41 and outlet end 51 of tube 43 are each open to a vacuum conduit 54. These connections could be made in any of a number of standard ways, including separate conduits connected to the tube ends 44–51 or a connection member attached to mounting plate 23 and having openings aligned with tube ends 44–51 and appropriate internal connections.

The vacuum conduit 54 connects outlet end 50 of tube 41 and outlet end 51 of tube 43 with induction bore 11 below mixing region 33 through a constant flow regulator 55, the function of which is to maintain a very constant mass flow rate in the air drawn through tubes 40–43 to the sub-atmospheric induction bore 11, since any variation in this flow rate will result in inaccuracy in the sensor output signal. The constant flow regulator 55 can be any standard device capable of accomplishing this task, the best example being a sonic or choked flow orifice in conduit 54. Since a choked flow orifice requires a larger vacuum on its downstream side than exists in mixing region 33, the conduit 54 is connected to the induction bore 11 below throttle 64, where vacuum is substantially greater except at wide open throttle, when a separate power enrichment system, not described herein, would presumably override the system of my invention.

A signal pressure tap 56 is provided between outlet end 48 of capillary tube 42 and inlet end 49 of capillary tube 41. Similarly, a signal pressure tap 57 is provided between outlet end 46 of capillary tube 40 and inlet end 47 of capillary tube 43. The capillary tubes 40–43 are thus seen to be connected in a bridge network with air being drawn at a constant mass flow rate through two parallel paths, one comprising tubes 42 and 41 and the other comprising tubes 40 and 43. Tubes in the same sensor conduit are arranged so that one is in the upstream leg of one path and the other is in the downstream leg of the other path, and each path contains a signal pressure tap between its upstream and downstream tubes. In operation, the sensor conduits 26 and 27 are both heated by the exhaust gases flowing past them to a temperature above the minimum activation temperature of the catalyst coating on the capillary tubes. With the catalyst thus active and excess air being mixed with the exhaust gases in sensor conduit 27, the variation with air-fuel ratio of the temperature of capillary tubes 40 and 41 will be different from that of capillary tubes 42 and 43.

Referring to FIG. 7, the variation with air-fuel ratio of capillary tubes 40 and 41 is shown as line 60. Maximum oxidation of combustible matter and the exhaust gases, and thus the maximum temperature reached by tubes 40 and 41, is achieved about stoichiometric. As the mixture deviates toward the lean side less carbon monoxide is available for oxidation; and as the mixture varies toward the rich side less oxygen is available. A scarcity of either carbon monoxide or oxygen slows the oxidation process and thus lowers the temperature.

The variation with air-fuel ratio of the temperature in tubes 42 and 43, however, is shown as line 61. This temperature variation is similar to that shown by line 60 on the lean side of stoichiometric except for a slight cooling effect due to the added air. However, on the rich side, the temperature rises sharply because of the oxidation due to the availability of extra oxygen along with the increased carbon monoxide. It happens that the intersection of lines 60 and 61, which indicates identical temperatures in each sensor conduit, occurs approximately at the desired operating point of the engine, slightly to the rich side of stoichiometric. Thus the differential exhaust temperature, obtained by subtracting line 60 from line 61, is indicated as dashed line 62, which crosses zero at the same air-fuel ratio at which lines 60 and 61 intersect. As is apparent from FIG. 7, there is a useful range of air-fuel ratios around the desired operating point in which the differential temperature shown in line 62 varies in a smooth and continuous manner with a continuously negative derivative which, in fact, roughly approximates a constant. The difference between the pressure measured at pressure tap 56 and a constant reference pressure is a pressure analogue of the differential temperature portrayed in line 62. The difference between the pressure at signal pressure signal tap 57 and the constant reference pressure is also a pressure analogue of differential temperature 62, but varying in the opposite direction. Therefore the differential pressure across the bridge network from tap 56 to tap 57 is also an analogue of the differential temperature 62; and an external constant reference pressure is unnecessary.

The air valve carburetor 10 will now be described with sufficient detail to show how the differential pressure between tap 56 and tap 57 can be utilized to vary the air-fuel ratio.

Referring to FIG. 1, the induction bore 11, already mentioned, contains two valves: a throttle valve 64, disposed in the usual manner on a throttle shaft 65; and an air valve 66, disposed upstream from throttle 64 on a valve shaft 67. Mixing region 33, already mentioned, is the volume between throttle valve 64 and air valve 66. A spring 68 is secured to downstream edge 70 of air valve 67 and extends to a bracket 71 to bias air valve 66 to the closed position shown. A tang 72 reaches upwardly from air valve 66 and is connected by a link 73 to a diaphragm 74. A chamber 75, formed between the right side of diaphragm 74 and a cover member 76, is connected by a tube 77 to mixing region 33.

A chamber 78, defined between the left side of diaphragm 74 and a cover member 79, is subjected to substantially atmospheric pressure, which is communicated to chamber 78 through openings 80 and 81.

In operation, chamber 75 is subjected to the sub-atmospheric pressure created in mixing region 33 as throttle valve 64 is opened, and diaphragm 74 acts through link 73 to pull air valve 66 clockwise to an open position. Spring 68, which does not appreciably change its force as air valve 66 opens, is effective to balance the opening force of diaphragm 74, thereby creating a substantially constant sub-atmospheric pressure in mixing region 33. By thus establishing a generally constant pressure drop across air valve 66, the area about air valve 66, and thus the rotative position of air valve 66, is determined by and is a measure of the rate of air flow through induction bore 11. A tab 82 extends upwardly from air valve 66 and is connected through a link 83 to one end 84 of a lever 85. The opposite end 86 of lever 85 is pivoted about a pin 87. Between ends 84 and 86, a hanger 88 extends from lever 85 into the carburetor fuel reservoir 13. The lower end 90 of hanger 88 has a hook 91 which is received in a recess 92 formed in a metering rod 93.

Metering rod 93 is disposed in a fuel passage 94 having its lower end 95 disposed to receive fuel from a well 96 formed in the bottom of the fuel reservoir 13. The upper end 97 of fuel passage 94 has an opening 98 through which fuel is discharged into mixing region 33. It will be appreciated, therefore, that the fuel in fuel reservoir 13 is subjected to a substantially constant metering head — from the substantially atmospheric pressure in the upper portion of the fuel bowl to the generally constant sub-atmospheric pressure in mixing region 33.

A metering jet or orifice 100 is disposed in fuel passage 94 around the tip 101 of metering rod 93. Metering rod 93 has flat tapered surfaces 102 on opposite sides which, upon reciprocation of metering rod 93 in jet 100, vary the area available for fuel flow through jet 100.

In operation, as air valve 66 opens by clockwise rotation, link 83 rotates lever 85 in a clockwise direction. Lever 85 then lifts hanger 88 to move metering rod 93 generally upwardly and rightwardly in fuel passage 94. Thus as air valve 66 is opened to increase the area available for air flow through air inlet 12, metering rod 93 is shifted to increase the area available for fuel flow through metering orifice 100. By this means, the air-fuel ratio may be maintained approximately constant with varying position of the throttle valve 64.

A spring 103 extends from a ledge 104 formed in fuel passage 94 to the lower end 105 of metering rod 93 to take up any slack in the linkage and to load metering rod 93 against jet 100.

A slot 106 is formed in the end 84 of lever 85. Link 83 is connected to lever 85 by having one end 107 disposed in slot 106. A link 108 extends from end 107 to an arm 110 of a supplementary lever 111 pivoted at 112. The opposite arm 113 of lever 111 is connected by a link 114 to one end 115 of an aneroid 116. The opposite end 117 of aneroid 116 is connected to a reciprocable plunger 118 threadedly received by an adjusting screw 119, guided in the bore 121 of an adjustable stop 122, and extended to a diaphragm 123.

A chamber 124 defined between the right side of diaphragm 123 and a cover member 125 is connected by means of a conduit 126 to signal pressure tap 57; while a chamber 127 defined between the left side of diaphragm 123 and a cover member 128 is connected by a conduit 129 to signal pressure tap 56. The sensor assembly is set up in such a way that the pressure at pressure tap 56 always exceeds the pressure at tap 57. The resulting rightward bias of diaphragm 123 is resisted by a spring 131 disposed between the head 132 of adjusting screw 119 and a support 133. The linkage is shown with the adjusting screw 119 biased away from the adjustable stop 122.

If the air-fuel ratio of the mixture supplied to the engine 15 varies to the lean side of the desired operating point, the temperature in sensor conduit 27 will decrease relative to that in sensor conduit 26. This will cause the pressure differential between taps 56 and 57, and thus across the diaphragm 123, to decrease, with a resulting leftward movement of diaphragm 123, plunger 118, aneroid 116, link 114 and arm 113 of the supplementary lever 111. This leftward movement is aided by spring 131 and another spring 134, extending between arm 113 and a fixed support 135. The counterclockwise rotation of supplementary lever 111 causes link 108 to move downward and reposition end 107 of link 83 in slot 106, whereby a shorter lever arm is defined between end 107 of link 83 and pivot pin 87. This increases the travel of metering rod 93 through metering jet 100 for equivalent opening movement of air valve 66 to provide an enriched air-fuel mixture. The adjustable stop 122 provides a limit to this enrichment, although it will not come into use most of the time during normal operation.

When the air-fuel ratio of the mixture supplied to engine 15 varies to the rich side of the desired operating point, the temperature in sensor conduit 27 increases with respect to that in sensor conduit 26; and the pressure differential between tap 56 and tap 57, and thus across diaphragm 123, increases. This causes rightward movement of the diaphragm 123, plunger 118, aneroid 116 and link 114 to rotate supplementary lever 111 in a clockwise direction. Link 108 accordingly raises the end 107 of link 83 in slot 106 to increase the length of the lever arm defined between link end 107 and pivot pin 87. This reduces the travel of metering rod 93 through metering jet 100 for equivalent opening movement of air valve 66 to provide a leaner air-fuel mixture.

Aneroid 116 provides correction for changes in ambient air pressure or ambient air temperature. Upon a decrease in the ambient air pressure or an increase in ambient air temperature, both indicative of a reduction in air density and consequently in the mass rate of air flow through air inlet 12 for equivalent volume air flow, aneroid 116 expands to force link 114 to the right and cause clockwise rotation of supplementary lever 111. This has the effect of decreasing the air-fuel ratio, which would otherwise be on the rich side due to the low air density.

Upon an increase in ambient air pressure or decrease in ambient air temperature, both indicative of an increase in air density, aneroid 116 contracts. Spring 134 then causes counterclockwise rotation of supplementary lever 111 to produce a richer air-fuel ratio, which would otherwise be too lean.

I claim:

1. For use with an internal combustion engine having means for inducting air and fuel in a variable ratio and engine exhaust means, apparatus for sensing air-fuel ratio of the engine exhaust gases and generating a signal for application to the air and fuel inducting means for controlling the ratio of air and fuel inducted in closed loop control, the apparatus comprising:
- a pair of sensor conduits within the exhaust means, each sensor conduit having an exhaust gas inlet orifice open in the exhaust means and an outlet, one of the sensor conduits having an air inlet orifice adjacent the exhaust gas inlet orifice and open to atmosphere;
- first, second, third and fourth capillary tubes having inlets and outlets and being coated on their outer surfaces with an oxidationn catalyst substance, the first and fourth capillary tubes being coadjacent within the one sensor conduit, the second and third capillary tubes being coadjacent within the other of the sensor conduits, the inlet of the second capillary tube communicating with the outlet of the first capillary tube, the inlet of the fourth capillary tube communicating with the outlet of the third capillary tube, and the inlets of the first and third capillary tubes being open to atmosphere;
- means for generating a substantially constant air pressure less than atmospheric, said means communicating with the outlets of the sensor conduits, whereby a metered flow of exhaust gas and air is drawn through the one sensor conduit over the first and fourth capillary tubes, a metered flow of exhaust gas is drawn through the other sensor conduit over the second and third capillary tubes, and the temperature of each tube is determined by the temperature of the gases flowing over it and the heat of catalytically induced chemical reactions adjacent its outer surface;
- means communicating with the outlets of the second and fourth capillary tubes for drawing air therethrough from the atmosphere through the first and third capillary tubes, said means including constant flow regulating means, whereby the pressure drop through each capillary tube is dependent on its temperature;
- a first signal pressure tap between the first and second capillary tubes; and
- a second signal pressure tap between the third and fourth capillary tubes, the pressure differential between the first and second signal pressure taps comprising a signal indicative of exhaust gas air-fuel ratio.

* * * * *